United States Patent [19]
Fehr et al.

[11] Patent Number: 5,530,183
[45] Date of Patent: Jun. 25, 1996

[54] SOYBEAN VARIETY 9253

[75] Inventors: Walter R. Fehr; Earl G. Hammond, both of Ames, Iowa

[73] Assignee: Iowa State University Research Foundation, Inc., Ames, Iowa

[21] Appl. No.: 378,896

[22] Filed: Jan. 25, 1995

Related U.S. Application Data

[63] Continuation of Ser. No. 179,409, Jan. 10, 1994, abandoned.

[51] Int. Cl.$^6$ .............................. A01H 4/00; A01H 5/00; A01H 5/10; C12N 5/04
[52] U.S. Cl. .................. 800/200; 800/255; 800/DIG. 26; 435/240.1; 435/240.4; 435/240.49; 435/240.5
[58] Field of Search .................................. 800/200, 250, 800/255, DIG. 26; 435/240.1, 240.4, 240.48, 240.49, 240.5; 47/58, DIG. 1

[56] References Cited

U.S. PATENT DOCUMENTS 5,024,944  6/1991  Collins et al. ...................... 435/172.3

OTHER PUBLICATIONS

Finer, John J. (1988) Apical proliferation of embryogenic tissue of soybean [*Glycine max* (L.) Merrill], *Plant Cell Reports*, 7:238–241.

Kim, et al. (1990) Plant Regeneration In vitro from Primary Leaf Nodes of Soybean (*Glycine max*) Seedlings, *J. Plant Physiol*, vol. 136, pp. 664–669.

Parrott, et al. (1989) Effect of genotype of somatic embryogenesis from immature cotyledons of soybean, *Plant Cell, Tissue and Organ Culture*, 16: 15–21.

Komatsuda, et al. (1991) Cell Biology & Molecular Genetics, *Crop Science*, 31:333–337.

Shoemaker, et al. (1988) Fatty Acid Composition of Soybean (*Glycine Max* (L.) Merr.) Somatic Embryos, *In Vitro Cellular & Developmental Biology*, vol. 24, No. 8, pp. 829–832.

Hammat, et al. (1987) Somatic Embryogenesis and Plant Regeneration from Cultured Zygotic Embryos of Soybean (*Glycine max* L. Merr.), *J. Plant Physiol.*, vol. 128, pp. 219–226.

Komatsuda, et al. (1990) Short Communication, Screening of Soybean [*Glycine max* L. Merrill] Genotypes of Somatic Embryo Production from Immature Embryo, *Japan J. Breed*, vol. 40, pp. 249–251.

Komatsuda, et al. (1988) Genotypes of high competence for somatic embryogenesis and plant regeneration in soybean *Glycine max*, *Theor. Appl. Genet.*, 75:695–700.

Lazzer, et al. (1987) Soybean somatic embryogenesis: Effects of hormones and culture manipulations, *Plant Cell, Tissue and Organ Culture 10*, 197–208.

Lazzer, et al. (1986) Soybean somatic embryogenesis: Effects of nutritional, physical and chemical factors, *Martinus Nijhoff Publishers, Dordrecht*, pp. 209–220.

Barwale, et al. (1986) Plant regeneration from callus cultures of several soybean genotypes via embryogenesis and organogenesis, *Planta*, 167: 473–481.

Spehar, et al. (1990) Clonal propagation of F1 hybrids as a tool in genetic studies of the soya bean [*Glycine max* (L.) Merrill], *Euphytica*, 47: 21–23.

Hepher, et al. (1988) Development of a Superficial Meristem During Somatic Embryogenesis from Immature Cotyledons of Soybean (*Glycine max* L.), *Annals of Botany*, 62: 513–519.

Buchheim, et al. (1989) Maturation of Soybean Somatic Embryos and the Transition of Plantlet Growth, *Plant Physiol.*, vol. 89, 768–775.

Christou, et al. (1989) Developmental Aspects of Soybean (*Glycine max*) Somatic Embryogenesis, *Annals of Botany*, vol. 64, pp. 225–234.

Hartweck, et al. (1988) Auxin–Orientation Effects on Somatic Embryogenesis from Immature Soybean Cotyledons, *In Vitro Cellular & Developmental Biology*, vol. 24, No. 8, pp. 821–828.

Wright, et al. (1986) Plant regeneration by organogenesis in *Glycine max*, *Plant Cell Reports*, 5: 150–154.

Ranch, et al. (1985) Plant regeneration from embryo–derived tissue cultures of soybeans, *In Vitro Cellular & Developmental Biology*, vol. 21, No. 11, pp. 653–658.

Parrott, et al. (1988) Optimization of somatic embryogenesis and embryo germination in soybean, *In Vitro Cellular & Developmental Biology*, vol. 24, No. 8, pp. 817–820.

Lazzeri, et al. (1988) Soybean somatic embryogenesis: interactions between sucrose and auxin, *Plant Cell Reports*, 7:517–520.

Shetty, et al. (1992) Stimulation of in vitro shoot organogenesis in *Glycine max* (Merrill.) by allantoin and amides, *Plant Science*, vol. 81, pp. 245–251.

Pandey, et al. (1992) Plant Regeneration from Leaf and Hypocotyl Explants of *Glycine wightii* (W. and A.) Verdc. var *longicauda*, *Japan J. Breed.*, 42: 1–5.

Komatsuda, et al. (1992) Maturation and germination of somatic embryos as affected by sucrose and plant growth regulators in soybeans *Glycine gracilis* Skvortz and *Glycine max* (L.) Merr., *Plant Cell, Tissue and Organ Culture*, 28: 103–113.

Stephens, et al. (1991) Agronomic evaluation of tissue–culture–derived soybean plants, *Theor. Appl. Genet.*, 82: 633–635.

Fournier, et al. (1991) Ultrastructural features of soybean somatic cells at the beginning of an organogenic process: toward a new concept, *Biol. Cell*, 73: 99–105.

Dhir, et al. (1992) Regeneration of fertile plants from protoplasts of soybean (*Glycine max* L. Merr.): genotypic differences in culture response, *Plant Cell Reports*, 11: 285–289.

Finer, et al. (1988) Development of an embryogenic suspension culture of soybean (*Glycine max* Merrill.), *Plant Cell, Tissue and Organ Culture*, 15: 125–136.

(List continued on next page.)

*Primary Examiner*—Gary Benzion
*Assistant Examiner*—Erich E. Veitenheimer
*Attorney, Agent, or Firm*—Burns, Doane, Swecker & Mathis

[57] ABSTRACT

Soybean variety 9253 is a high-performance soybean variety which also provides a low linolenic acid specialty soybean oil.

6 Claims, No Drawings

OTHER PUBLICATIONS

Ranch, et al. (1986) Plant Regeneration from Tissue Cultures of Soybean by Somatic Embryogenesis, *Cell Culture and Somatic Cell Genetics of Plants*, vol. 3, pp. 97–110.

Lazzeri, et al. (1985) A Procedure for Plant Regeneration from Immature Cotyledon Tissue of Soybean, *Plant Molecular Biology Reporter*, vol. 3, No. 4, pp. 160–167.

Sebastian, et al. (1985) "Efficient Selection for Brown Stem Rot Resistance in Soybeans Under Greenhouse Screening Conditions", *Crop Sci.*, 25: 753–757.

S 28–18 In Northrup King Seed Guide, 1991 (Apr.) p. 34 (West Central Ed.).

S 23–12 In Northrup King Seed Guide, 1991 (Apr.) p. 43 (Northern Ed.).

S 42–30 In Northrup King Seed Guide, 1991 (Apr.) p. 25 (Mid–South Ed.).

Nelson, et al. (1989) "Evaluating Soybean Germ Plasm for Brown Stem Rot Resistance", *Plant Disease*, 73: 110–114.

Ill. Agri. Exper. Station, (1991) Release Notice for L84–5873 and L84–5932.

Germplasm Resources Information Network (GRIN), (1994) USDA, Beltsville MD Printout from Database.

Athow, Kirk L. (1985) Phytophthora Root Rot of Soybean, *In World Soybean Research Conference III: Proceedings*, Shibles, et al., Westview Press, pp. 575–581.

Bernard, et al. (1988) Registration of Crop Cultivars, *Crop. Sci.*, 28: 1027.

PVP No. 7900064, Soybean Sloan, Issued 1980.

Burton, J. W. (1987) Quantitative Genetics: Results Relevant to Soybean Breeding, In Soybeans: Improvement Production and Uses Monograph No. 16. ASA Publisher, pp. 211–247.

Fehr, Walter R. (1987) Breeding Methods for Cultivar Development, *In Soybeans: Improvement Production and Uses Monograph No. 16*, ASA Publisher, pp. 249–293.

Lersten, et al. (1987) Vegetative Morphology, *In Soybeans: Improvement Production and Uses Monograph No. 16*, ASA Publisher, pp. 49–94.

Carlson, et al. (1987) Reproductive Morphology, *In Soybeans: Improvement Production and Uses Monograph 16*, ASA Publisher, pp. 95–133.

Evans, D. A. (1981) Campbell Institute for Research and Technology, Soybean Genetics Newsletter, 8: 27–29.

Palmer, Reid G. (1987) Qualitative Genetics and Cytogenetics, *In Soybeans: Improvement Production and Uses Monograph No. 16*, ASA Publisher, pp. 135–143.

Rieger et al. 1976. Glossary of Genetics and Cytogenetics. Classical and Molecular. p. 256.

Fehr. 1980. In Hybridization of Crop Plants. Fehr et al., eds. p. 592.

Wilcox et al. 1986. Crop Science. 6: 209–210.

Barwale et al, 1987. Plant Cell Reports, 6:365–368.

Luedders. 1977. Crop Science. 17:971–972.

Palmer et al. 1987. In Soybeans: Improvement, Production, and Uses. 2nd ed. Wilcox, ed. Ch 5: 135–209.

SOYBEAN VARIETY 9253

This application is a continuation of application Ser. No. 08/179,409, filed Jan. 10, 1994, now abandoned.

FIELD OF THE INVENTION

This invention is in the field of plant breeding, specifically soybean breeding.

BACKGROUND OF THE INVENTION

The soybean is a commercially very important plant which has an extraordinary number and variety of uses. It is used as a source of both food for domestic animals and human beings, and as a source of oil, which itself has many important uses. The soybean cake or meal, that remains after processing the beans for oil, is a high-protein foodstuff used extensively in livestock and poultry rations. It is an excellent protein with respect to most of the essential amino acids and also a good source of vitamins of the B-complex. The botanical name for the soybean is *Glycine max*, the genus to which the variety belongs being identified by the first Latin word and the species to which it belongs by the second Latin word.

The soybean is an annual summer legume, and is, like other members of the botanical family Leguminosae such as peas and beans, characterized by having pods each of which (in the case of the soybean) has from 2 to 4 round or oval seeds (beans). Soybeans are classified as simple fruits since they are derived from a single ovary, and can be reproduced from single seeds contained within a pod of the plant. Classification structure and nature of legumes is described by Robbins et al., *Botany: An Introduction to Plant Science*, John Wiley & Sons, Inc. (1950).

The soybean is an erect, branching plant, with trifoliate leaves borne one to a node, resembling in its early growth the ordinary field bean. It grows to a height ranging from 2 ft. to 3½ ft. or more. Nearly all varieties are pubescent; that is, the stems, leaves and pods of the plant are covered with short, fine, brown or gray hairs. The mature pods range in color from very light tan to shades of gray, brown and black, and the seeds themselves may be colored in shades of yellow, green, brown or black, or may be speckled. The seeds have an oil content ranging from 15% to 25%, and a protein content ranging from 30% to 50%.

There are a number of ways in which soybeans may be classified, including by color, plant type, plant habit, and seed characteristics.

Color: Soybeans have leaves which range in color from light green to dark green; the pod color may range anywhere from light tan to black, as aforesaid; and the seed coat color may range from yellow to black. Finally, the pubescence color may be either gray or brown.

Plant Type: Soybeans may also be classified as slender, bushy or intermediate.

Plant Habit: Soybeans may be classified, as regards habit, as being determinate or indeterminate.

Seed Characteristics: The seeds of soybeans may be characterized according to shape—whether they are spherical or elongate—and according to size; and also according to whether they are wrinkled or smooth.

A mature soybean plant comprises roots, stems, petioles, leaflets, pods and seeds. Prior to maturity a soybean plant has small inconspicuous flowers, which may be either white or purple.

DEFINITIONS

As used in this disclosure the following terms have the following meanings:

HABIT: The physical appearance of a plant. It can be either determinate or indeterminate. In soybeans indeterminate varieties are those in which stem growth is not limited by formation of a reproductive structure (i.e., flowers, pods and seeds) and hence growth continues. The main stem will develop and set pods over a prolonged period under favorable conditions.

POD: Is the fruit of a soybean plant. It consists of the hull or shell and the soybean seeds.

LEAFLETS: Are part of the plant shoot, and they manufacture food for the plant by the process of photosynthesis.

SHOOTS: A portion of the body of the plant. They consist of stems, petioles and leaves.

HILUM: The scar left on the seed which marks the place where the seed was attached to the pod prior to it (the seed) being harvested.

COTYLEDON: A seed leaf; a small leaf contained on a plant embryos. The cotyledon contains the food storage tissues of the seed. The embryo is the small plant contained within a mature seed.

PUBESCENCE: A covering of very fine hairs closely arranged on the leaves, stems and pods of the soybean plant.

HYPOCOTYL: That portion of an embryo or seedling between the cotyledons and the radicle or young root.

PLANT HEIGHT: Is the distance from the surface of the soil in which the plant is growing to the top of the plant at maturity.

PHYTOPHTHORA: A fungus which causes root rot of soybeans, as well as other plant diseases.

MATURITY GROUP: An agreed-on industry break out of groups of varieties, based on the zones in which they are adapted primarily according to day length or latitude. They consist of very long day length varieties (Groups 000, 00, 0), and extend to very short day length varieties (Groups VII, VIII, IX, X).

MATURITY: That stage in development of the soybean plant when its physiological development is complete. The period from the beginning of growth until maturity is reached is measured in days, usually in comparison to one or more standard varieties. This trait is normally determined as the time when 95 percent of the plant's pods are fully mature.

$F_3$: Denotes a generation resulting from the selfing of the $F_2$ generation along with selection for type and rogueing of off-types. The "F" number is a term commonly used in genetics, and designates the number of the filial generation. The "$F_3$" generation denotes the offspring resulting from the selfing or self mating of members of the generation having the next lower "F" number, viz. the $F_2$ generation.

DETAILED DESCRIPTION OF THE INVENTION

This soybean variety was developed from the cross between Conrad X and FA4737EMS-119. It is an BC2F3-derived variety which was first grown in yield trials in 1990 by Iowa State University.

Subsequently, this variety has undergone two additional years of extensive evaluation by Pioneer Hi-Bred International, Inc., Des Moines, Iowa 50309 (Pioneer) for agronomic traits, wide area adaptability, and fatty acid composition. 1.8 acres of increase seed were grown in Chile during the winter of 1991–92 by Pioneer. 83 acres of parent seed stock (foundation seed equivalent) were grown in Iowa in 1992. Pioneer, which plans to sell the variety to the public in 1994, has given this variety the denomination "9253". 9253 has been observed by the breeders to be uniform and stable for all plant traits from generation to generation, with no evidence of variants.

Variety 9253 can be produced from seed thereof by the conventional methods well known in the art for producing and harvesting soybeans. Soybean is highly self-pollinated and no special procedures with regard to pollination are necessary. The seed is planted and grown under conventional conditions. Seed from every plant which produces seed can be harvested.

Soybean variety 9253 is most similar to variety 9273. Both varieties have purple flowers, tawny pubescence and yellow seeds. However 9253 has brown hila, tan pods, and at most about a 3.5% linolenic acid content in its seeds, whereas 9273 has black hila, brown pods, and 8.4% linolenic acid content in its seeds, representing a substantial decrease in linolenic acid content. Thus, this variety is a specialty oil variety which can be crushed to provide a low linolenic soybean oil having less than 3.5% linolenic acid content, while conventional commodity soybean oil has over 4%, and typically up to 9 or 10%, linolenic acid content. Such low linolenic oil is highly preferred for its greater stability under storage and frying conditions and thus provides the grower an opportunity to realize a price premium over conventional commodity soybeans. This benefit is provided in a germplasm background in which the variety as a whole presents no "production drag" by virtue of the presence of the specialty trait, i.e., its agronomic performance is comparable to other commercial varieties grown in its region of adaptation, which is primarily Iowa, and especially Northern Iowa. As a result, the financial premium this variety offers is real, since the higher price obtained for the grain is generally not offset by a reduction in yield. In addition, its low linolenic content is optimized (i.e., pushed toward the low end of its 2.5% to 3.5% linolenic acid range) under management practices in which it is planted early and grown in a warmer season, since cold stress tends to favor production of triglycerides containing unsaturated fatty acids. Finally, its greater lodging tendency means that it can be grown to best advantage on lower productivity soils, offering an additional benefit to the grower in terms of optimizing his production.

These and other objective characteristics of variety 9253 are set forth in the following table:
SEED SHAPE: elongated.
SEED COAT LUSTER AND COLOR: dull yellow
SEED SIZE: 19 grams per 100 seeds
HILA COLOR: brown.
COTYLEDON COLOR FOR THE MATURE SEED: yellow.
SEED PEROXIDASE ACTIVITY: HIGH
SEED PROTEIN ELECTROPHORETIC BANDS: Not tested.
HYPOCOTYL COLOR: light purple (same as public varieties Beeson and Pickett 71.)
LEAFLET SIZE AND SHAPE: medium ovate
LEAF COLOR: medium green (similar to the public varieties Corsoy 79' and Braxton).
FLOWER COLOR: purple
POD COLOR: tan
PLANT PUBESCENCE COLOR: gray
PLANT TYPE: INTERMEDIATE between slender and bushy
PLANT HABIT: indeterminate
MATURITY GROUP: Group II
DISEASE REACTIONS:
 BROWN STEM ROT—resistant
 PHYTOPHTHORA ROT RACES 10, 12, 13, 16, 17, 19, 20, 21 AND 25-susceptible
PHYSIOLOGICAL RESPONSES
 IRON CHLOROSIS—susceptible in calcareous soil
 METRIBUZIN RESISTANCE—resistant
INSECT REACTION RESPONSES
 Not tested Certain characteristics of variety 9253 have been compared with the characteristics of the variety 9273 as set forth in the following table:

|  | 9253 | 9273 |
| --- | --- | --- |
| Days to Maturity | 131 | 131 |
| Lodging Score | 2.8 | 1.8 |
| Plant Height | 93 cm | 86 cm |
| Seed Protein Content | 42% | 42.4% protein |
| Oil Content | 19.0% | 20.4% |
| Seed Size | 19.0 grams | 19.0 grams |

TISSUE CULTURE AND REGENERATION

Tissue culture of various tissues of soybeans and regeneration of plants therefrom is well known and widely published. For example, reference may be had to Lazzeri, P. et at., "A Procedure for Plant Regeneration from Immature Cotyledon s Tissue of Soybean", *Plant Molecular Biology Reporter*, 3(4), 160 (1985); Ranch, J. P. et al., "Plant Regeneration from Embryo-Derived Tissue Cultures of Soybeans," *In Vitro Cellular & Developmental Biology*, 21(11):653–658 (1985); Barwale, U. B., et al., "Plant regeneration from callus cultures of several soybean genotypes via embryogenesis and organogenesis," Planta (1986) 167:473–481; Ranch, J. P. et at., "Plant Regeneration from Tissue Cultures of Soybean by Somatic Embryogenesis", in *Cell Culture and Somatic Cell Genetics of Plants*, Vol. 3, Chapt. 4 (Academic Press, 1986); Wright, M. S., et at., "Plant regeneration by organogenesis in *Glycine max*," Plant Cell Reports (1986) 5:150–154; Hammatt, N. et al., "Somatic Embryogenesis and Plant Regeneration from Cultured Zygotic Embryos of Soybean (Glycine max L. Merr.)," J. Plant Physiol. 128:219–226 (1987); Lazzeri, P. A. et al., "Soybean somatic embryogenesis: Effects of hormones and culture manipulations," *Plant Cell, Tissue and Organ Culture*, 10:197–208 (1987); Lazzeri, P. A. et al., "Soybean somatic embryogenesis: Effects of nutritional, physical and chemical factors," *Plant Cell, Tissue and Organ Culture*, 10:221–226 (1987); Finer, J. et al., "Development of an embryogenic suspension culture of soybean (Glycine max Merrill)," *Plant Cell. Tissue and Organ Culture*, 15:125–136 (1988); Finer, J., "Apical proliferation of embryogenic tissue of soybean [Glycine max (L.) Merrill]," Plant Cell Reports (1988) 7:238–241; Hartweek, L. M. et al., "Auxin-Orientation Effects on Somatic Embryogenesis from Immature Soybean Cotyledons," *In Vitro Cellular & Developmental Biology*, 24(8):821–828 (1988); Hepher, A. et al., "Development of a Superficial Meristem During Somatic Embryogenesis from Immature Cotyledons of Soybean (Glycine max L.)," Annals of Botany 62:513–519 (1988); Komatsuda, T. et al., "Genotypes of high competence for somatic embryogenesis and plant regeneration in soybean *Glycine max*," *Theor. Appl. Genet*, (1988) 75:695–700; Lazzeri, P. A., "Soybean somatic embryogenesis: interactions between sucrose and auxin," Plant Cell Reports (1988) 7:517–520; Parrott, W. A. et al., "Optimization of Somatic Embryogenesis and Embryo Germination in Soybean," *In Vitro Cellular & Developmental Biology*, 24(8):817–820 (1988); Buchheim, J. A. et al., "Maturation of Soybean Somatic Embryos and the Transition to Plantlet Growth," *Plant Physiol*, (1989) 89, 768–775; Christou, P. et al., "Developmental Aspects of Soybean (Glycine max) Somatic Embryogenesis," *Annals of Botany*, 64, 225–234 (1989); Parrott, W. A. et al., "Effect of genotype on somatic embryogenesis from immature cotyledons of soybean," *Plant Cell, Tissue and Organ Culture* 16:15–21 (1989); Kim, J. et al., "Plant Regeneration In Vitro from Primary Leaf Nodes of Soybean (Glycine max) Seedlings," *J, Plant Physiol.*, 136:664–669 (1990); Komatsuda, T. et al., "Screening of Soybean [*Glycine max* (L.) MERRILL] Genotypes for Somatic Embryo Production from Immature Embryo," *Japan J. Breed.* 49:249–251 (1990); Spehar, C. R. et al., "Clonal propagation of $F_1$ hybrids as a tool in genetic studies of the soya bean [*Glycine max* (L.) Merrill]," Euphytica, 47:21–23 (1990); Komatsuda, T. et al., "Genotype X Sucrose Interactions for Somatic Embryogenesis in Soybean," *Crop Sci*, 31:333–337 (1991); Stephens, P. A. et al., "Agronomic evaluation of tissue-culture-derived soybean plants," *Theor. Appl. Genet.* (1991) 82:633–635; Komatsuda, T. et at., "Maturation and germination of somatic embryos as affected by sucrose and plant growth regulators in soybeans *Glycine gracilis* Skvortz and *Glycine max* (L.) Merr.," *Plant Cell, Tissue and Organ Culture*, 28:103–113 (1992); Dhir, S. et al., "Regeneration of fertile plants from protoplasts of soybean (Glycine max L. Merr.): genotypic differences in culture response," *Plant Cell Reports* (1992) 11:285–289; Pandey, P. et al., "Plant Regeneration from Leaf and Hypocotyl Explants of Glycine wightii (W. and A.) VERDC. var longicauda," *Japan J. Breed.* 42:1–5 (1992); and Shetty, K., et al., "Stimulation of in vitro shoot organogenesis in Glycine max (Merrill.) by allantoin and amides," Plant Science 81:(1992) 245–251; as well as U.S. Pat. No. 5,024,944, issued Jun. 18, 1991 to Collins et al. and U.S. Pat. No. 5,008,200, issued Apr. 16, 1991 to Ranch et at., the disclosures of which are hereby incorporated herein in their entirety by reference. Whole fertile plants of 9253 can be readily regenerated from such tissue culture and a high percentage of such plants will also have the 9253 genotype and will produce true-breeding seed of the 9253 variety.

DEPOSITS

A viable deposit of the soybean seed of this invention is maintained by Pioneer Hi-Bred International, Inc., 700 Capital Square, 400 Locust Street, Des Moines, Iowa 50309, as well as at Iowa State University, Ames, Iowa 50011. Access to this deposit will be available during the pendency of this application to persons determined by the Commissioner of Patents and Trademarks to be entitled thereto under 37 CFR 1.14 and 35 USC 122. Upon the grant of the present patent, Applicants will make available to the public without restriction a viable deposit of at least 2500 seeds of soybean variety 9253 with the American Type Culture Collection (ATCC), Rockville, Md. 20852, U.S.A., ATCC Deposit No. 97415. Such deposit was made under the Budapest Treaty in the ATCC on Jan. 16, 1996. The seeds deposited with the ATCC have been taken from the same deposit maintained by Iowa State University, Ames, Iowa 50011 since prior to the filing date of this application. The deposit will be maintained at the ATCC Depository, which is a public depository, for a period of 30 years, or five years after the most recent request, or for the enforceable life of the patent, whichever is longer, and will be replaced if it becomes nonviable during that period.

What is claimed is:

1. Seed of the soybean variety designated as 9253, deposited as ATCC Deposit No. 97415.

2. A plant produced by a seed of the soybean variety designated as 9253, deposited as ATCC Deposit No. 97415.

3. A culture of regenerable tissue of a plant produced by a seed of the soybean variety designated as 9253, deposited as ATCC Deposit No. 97415.

4. A culture according to claim 3, wherein the tissue is selected from the group consisting of leaves, pollen, embryos, meristems, roots, root tips, flowers, beans, pods, and stalks, and cells and protoplasts thereof.

5. A soybean plant regenerated from a culture of regenerable tissue of a plant produced by a seed of the soybean variety designated as 9253, deposited as ATCC Deposit No. 97415, having all of the physiological and morphological characteristics of soybean variety 9253.

6. A culture of regenerable tissue of a soybean plant, said soybean plant having all of the physiological and morphological characteristics of soybean variety 9253, wherein said soybean plant is regenerated from a culture of regenerable tissue of a plant produced by a seed of the soybean variety designated as 9253, deposited as ATCC Deposit No. 97415.

* * * * *